United States Patent
Kim et al.

(10) Patent No.: US 12,118,719 B2
(45) Date of Patent: Oct. 15, 2024

(54) SYSTEM AND METHOD FOR PREDICTION OF DISEASE PROGRESSION OF PULMONARY FIBROSIS USING MEDICAL IMAGES

(71) Applicant: The Regents of the University of California, Oakland, CA (US)

(72) Inventors: Hyun Kim, Los Angeles, CA (US); Yu Shi, Fremont, CA (US); Jonathan Gerald Goldin, Oakland, CA (US); Weng Kee Wong, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 407 days.

(21) Appl. No.: 17/639,511

(22) PCT Filed: Sep. 3, 2020

(86) PCT No.: PCT/US2020/049099
§ 371 (c)(1),
(2) Date: Mar. 1, 2022

(87) PCT Pub. No.: WO2021/046152
PCT Pub. Date: Mar. 11, 2021

(65) Prior Publication Data
US 2022/0327693 A1 Oct. 13, 2022

Related U.S. Application Data

(60) Provisional application No. 62/895,496, filed on Sep. 3, 2019.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0037* (2013.01); *A61B 5/7267* (2013.01);
(Continued)

(58) Field of Classification Search
CPC ......... G06T 7/0012; G06T 2207/10081; G06T 2207/30101; G06T 2207/10116;
(Continued)

(56) References Cited

U.S. PATENT DOCUMENTS

2012/0329666 A1  12/2012  Steele et al.
2015/0351714 A1* 12/2015  De Backer ........... A61B 5/7246
                                               600/407
(Continued)

OTHER PUBLICATIONS

European Patent Office, Extended Search Report, Application No. 20861499.0, Aug. 8, 2023, 9 pages.
(Continued)

*Primary Examiner* — Neil R McLean
(74) *Attorney, Agent, or Firm* — Quarles & Brady LLP

(57) ABSTRACT

A method for training a machine learning algorithm that classifies predictive regions-of interest ("ROI") of progression of idiopathic pulmonary fibrosis. The method includes acquiring a set of computed tomography (CT) images of a plurality of patients and selecting a plurality of ROIs within the set of images. Each of the ROIs designates a label that indicates progression of pulmonary fibrosis and training a machine learning algorithm by inputting the plurality of ROIs and the associated labels into the algorithm. The algorithm identifies the ROIs in the set of images as indicating regions of pulmonary fibrosis within the set of images based on the features.

15 Claims, 6 Drawing Sheets

(51) Int. Cl.
*A61B 6/00* (2006.01)
*A61B 6/03* (2006.01)
*G06V 10/25* (2022.01)
*G06V 10/77* (2022.01)

(52) U.S. Cl.
CPC ............ *A61B 5/7275* (2013.01); *A61B 6/032* (2013.01); *A61B 6/5217* (2013.01); *G06V 10/25* (2022.01); *G06V 10/7715* (2022.01); *G06T 2207/10081* (2013.01); *G06T 2207/30101* (2013.01); *G06V 2201/03* (2022.01); *G06V 2201/07* (2022.01)

(58) Field of Classification Search
CPC . G06T 2207/20081; G06T 2207/20084; G06T 2207/30061; G06T 7/0016; A61B 5/0037; A61B 5/7267; A61B 5/7275; A61B 6/032; A61B 6/5217; A61B 6/02; A61B 6/469; A61B 5/08; G06V 10/25; G06V 10/7715; G06V 2201/03; G06V 2201/07; G06N 3/048; G06N 20/10; G06N 3/006; G06N 3/126; G06N 5/01; G06N 20/20; G16H 15/00; G16H 30/40; G16H 40/63; G16H 40/67; G16H 50/20; G16H 50/30; G16H 50/70
USPC ........................................................ 382/131
See application file for complete search history.

(56) References Cited

U.S. PATENT DOCUMENTS

| | | |
|---|---|---|
| 2017/0010456 A1 | 1/2017 | Gopinath et al. |
| 2017/0247759 A1 | 8/2017 | Wilde et al. |
| 2017/0261584 A1 | 9/2017 | James et al. |
| 2018/0061049 A1* | 3/2018 | Robb ................... A61B 6/5217 |

OTHER PUBLICATIONS

PCT International Search Report and Written Opinion, PCT/US2020/049099, Nov. 13, 2020, 14 pages.
Shi, Y. et al., Artificial Intelligence in Medicine 100 (2019) 101709, 10 pages.

* cited by examiner

Algorithm 1 QPSO-RF Alorigthm

Input: a data set S, a feature set F, pre-fixed parameters including number of particles p, dimension of the particles d, maximum iteration number $max_{iter}$ and random forest H as a learning algorithm. Set QPSO parameters as: $max_{iter} = 1000$, $p = 40$, and $d = 71$. Additionally, set RF parameters as: the number of trees B=100, the maximum depth of each tree = 20 and the proportions of subsample from the data set = 0.5.

Output: a feature subset $F_S$ that gives the best fitness value.

Resampling: use SMOTE algorithm to resample the training set.
    Initialization of QPSO: randomize binary bits for particles, particles' personal best (pbest) and swarm's global best (gbest). Twelve steps are the procedure of QPSO-RF, where RF is nested into each iteration of QPSO.

1: for iter $\leq max_{iter}$
2. for $t \leq p$
3. Perform mutation operation on each particle.
4. Determine the mean best (mbest) for each particle x at dimension d:

$$m_d^{best} \begin{cases} 1, 1/p \ \Sigma P \ x_i, d^{pbest} > 0.5 \\ 0, 1/p \ \Sigma P \ x_i, d^{pbest} < 0.5 \\ 1, \text{with prob} = 0.5, 1/p \Sigma P x_i, d^{pbest} = 0.5 \end{cases}$$

5. Select one of the offspring randomly.
6. For each dimension, flip the particle with mutation probability defined by $$\min(1/p \ \beta \ d_H(x_i, x^{mbest}) \ in 1/u, 1),$$

where $d_H$ are the counts of different bits in the two strings, u ~unif(0,1) and $\beta$ is a tuning parameter set to decrease from 1.4 to 0.4 over the iterations. The decreasing values of $\beta$ allow more localized search as the swarm evolves.

7. On the resampled training set, evaluate each particle using random forest:
8. Start with an empty forest H.
9. for $i \leq B$
10. Bootstrap a subsample from S.
11. At each node, split on the best feature represented by the particle. Save the tree $h_i$ learned from this feature subset.
12. Add $h_i$ to H.
    endfor return minimum of sensitivity and specificity from H. Each particle is evaluated using this metric: update
        pbest as the best feature subset one particle visited so far and gbest as the best feature subset of the
        swarm visited so far.
    endfor
endfor
return gbest vector that represent the best feature subset, which has maximum min(sensitivity, specificity).

FIG. 4

SYSTEM AND METHOD FOR PREDICTION OF DISEASE PROGRESSION OF PULMONARY FIBROSIS USING MEDICAL IMAGES

CROSS-REFERENCE TO RELATED APPLICATIONS

This application represents the national stage entry of PCT/US2020/049099 filed on Sep. 3, 2020 and claims the benefit of U.S. Provisional Patent Application Ser. No. 62/895,496 filed on Sep. 3, 2019 and entitled "System and Method for Prediction of Disease Progression of Pulmonary Fibrosis Using Medical Images," the contents of which is incorporated herein by reference as if set forth in its entirety for all purposes.

STATEMENT REGARDING FEDERALLY SPONSORED RESEARCH

This invention was made with government support under Grant Number R21 HL123477-01A1 awarded by the National Institutes of Health. The government has certain rights in the invention.

BACKGROUND

Idiopathic Pulmonary Fibrosis ("IPF") is a chronic irreversible and ultimately fatal disease of unknown etiology. It is characterized by an unpredictable progressive decline in lung function and typically affects people in the age group of 50-70 years. The median survival time for a patient with IPF is approximately 3.8 years. IPF exhibits a highly heterogeneous natural history, and the disease progression is unpredictable at the time of diagnosis: some subjects may experience episodes of acute respiratory worsening despite being previously stable. It is critically important to distinguish subgroups of IPF subjects who are expected to progress from those who are expected to remain stable. The identification helps clinicians to make a decision about continuing or switching a treatment, or to refer for lung transplantation at an early stage.

Computed tomography and, in particular, High-resolution Computed Tomography ("HRCT") plays an important role in the diagnosis of IPF. Studies have shown that HRCT features are useful and sensitive in predicting progression in IPF subjects based on the patterns changes of usual interstitial pneumonia ("UIP") between two scans. Research shows that UIP patterns on HRCT are associated with high mortality and disease progression in subjects with IPF. Features extracted from HRCT images are high-dimensional, which pose a challenge for image recognition systems because redundant or non-informative features sometimes reduce classification accuracy.

Machine Learning and Deep Learning are part of medical imaging applications in Artificial Intelligence (AI), which gained research attention before the mid-1980s. However, the reproducibility, generalizability, and computational power hamper the broadening usage of AI. A report from the Institution of Medicine clarifies the pathway of Omic-based for an algorithmic development and evaluation, which emphasizes the repeatability and reproducibility using separate training sets for algorithm development from independent tests for clinical validation and utilization in the translational medicine. Generally, there are three steps in an algorithm pathway: (1) model development, (2) analytic validation, and (3) clinical validation. Statistical design of the frame in training and the test set, along with the metrology in reporting reproducibility results, can play an important pathway of developing a robust machine or deep learning algorithm.

Machine learning includes supervised learning and unsupervised learning. In supervised learning, an expert provides a ground truth or reference at the time of imaging for model development and evaluation, whereas in unsupervised learning a model is first built, such as by using a clustering approach, and then evaluated using an external truth, such as clinical outcomes. Medical imaging is one of many applications of using a supervised learning with feature selection and classification for multi-features (i.e. multi-variables).

Therefore, a system and method is needed to assist clinicians with tracking the progress of diseases, such as IPF, and assisting clinicians with predicting progression of such diseases, including IPF. Given the importance of early treatment decisions, there also remains a need for a machine learning approach able to predict progression from medical images for IPF.

SUMMARY OF THE DISCLOSURE

The present disclosure addresses the aforementioned drawbacks by providing systems and methods for the prediction of disease progression, such as idiopathic pulmonary disease, based on the evaluation of medical images using a machine learning method. The present disclosure provides a feature selection procedure to select a subset of important HRCT features to stratify the groups of subjects who are likely to progress or not.

In one aspect, a system is provided that classifies predictive region-of-interest ("ROIs") of progression of idiopathic pulmonary fibrosis. The system includes a processor configured to analyze images of a patient and indicate regions in the images expected to reflect progressive pulmonary fibrosis in the future using a machine learning algorithm. The system also includes a display to communicate the image of the patient indicating the regions in the images expected to reflect progressive pulmonary fibrosis in the future and a memory accessible by the processor and having stored thereon the machine learning algorithm. The machine learning algorithm having been trained by: (a) acquiring a set of computed tomography (CT) images of a plurality of patients; (b) selecting a plurality of ROIs within the set of images that designate a label indicating progression of pulmonary fibrosis; (c) training the machine learning algorithm by inputting the plurality of ROIs and the associated labels into the machine learning algorithm, which identifies the ROIs in the set of images as indicating regions of pulmonary fibrosis within the set of images based on the features; and (d) generating classification probabilities from the output of the machine learning algorithm that classifies regions in the set of images as indicating regions of expected to be progressive pulmonary fibrosis in the future within the set of images.

In another aspect, the present disclosure provides a method for generating a report that classifies and quantitatively detects progression of idiopathic pulmonary fibrosis. The method can include acquiring a computed tomography (CT) image, and subjecting the image to a machine learning algorithm. The machine learning algorithm can be created by acquiring a set of CT images of a plurality of patients, selecting a plurality of ROIs within the set of images, inputting the plurality of ROIs and the associated features into the algorithm, and generating quantitative probabilistic parameters as an output of the machine learning algorithm.

Each of the ROIs can designate an associated label that indicates progression of pulmonary fibrosis. The method of generating a report further can include generating probability parameters by evaluating the quantitative parameters, using only the first set of images. The probability parameters can predict progression of idiopathic pulmonary fibrosis. The method also includes generating a report from the probability parameters and the quantitative parameters using the computer system. The report indicates a quantitative analysis of the progression of idiopathic pulmonary fibrosis.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 4 shows the steps of an example algorithm for training a machine learning algorithm according to some embodiments described in the present disclosure.

DETAILED DESCRIPTION

Figure 1A:
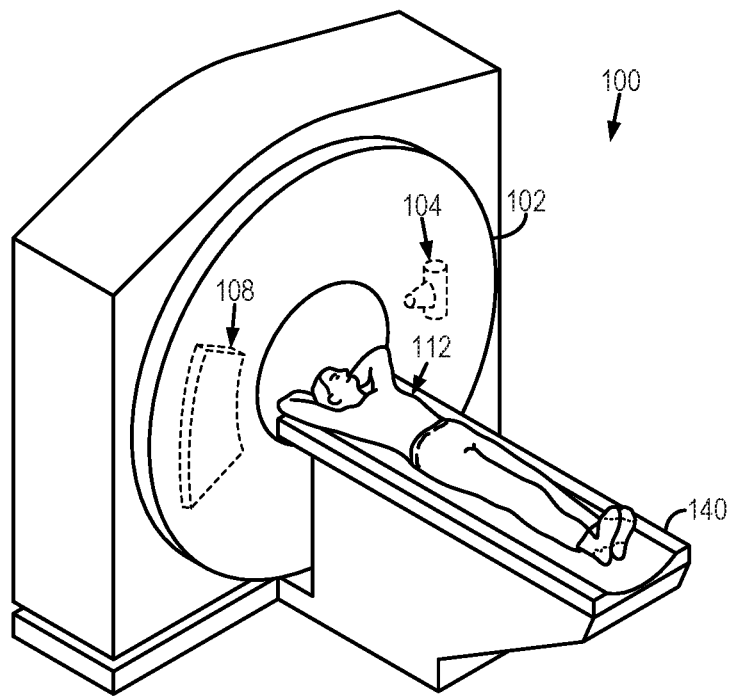
FIGS. 1a and 1b are a block diagram of an example computed tomography ("CT") system that can implement the methods described in the present disclosure.

Described here are systems and methods for detecting progression of disease, such as by training a machine learning algorithm, and using the trained machine learning algorithm to detect the progression of the disease in an image. In a non-limiting example, a disease is idiopathic pulmonary fibrosis ("IPF") and a machine learning algorithm may detect the progression or stabilization of IPF in an image. With effective anti-fibrotic IPF therapeutic treatments now being available, there is an increasing need to understand the early signs of improvement or stabilization, not only progression.

Several methods have been proposed to select features and build classification models in the medical imaging field. Regularization methods of selecting features, such as least absolute shrinkage and selection operator ("LASSO") and smoothly clipped absolute deviation ("SCAD"), are handy and popular methods in the field. The field of classification has seen increasing uses of more advanced techniques, such as random forest, support vector machine ("SVM"), neural network ("NNET"), etc. However, these methods have no feature selection, or separate the feature selection and classification, which fail to select the optimized feature subset that leads to the best classification performance.

An appropriate approach to integrate feature selection and classification is a wrapper method, which directly uses the classification performance of a given model to assess selected subsets of features. Efficient search strategies may be used for a wrapper method to identify the best feature subset. Evolutionary computation ("EC") includes an advantage of good global optimization properties and is employed by many state-of-the-art EC-based feature selection techniques. Compared with traditional searching methods, EC techniques do not need domain knowledge and do not make any assumptions about the feature space, such as linear separability and differentiability. EC is particularly useful because the objective function does not have an analytical form, and the common optimization techniques, which require leveraging mathematical properties of the objective function, cannot be used.

The methods described herein include a study design of collecting a data set with ground truth for prediction via visual registration by a radiologist; and the development of an objective metric and an algorithm that simultaneously achieves high prediction accuracy, balanced sensitivity and specificity with a parsimonious feature subset, using a relatively small number of subjects.

In one embodiment, the method can use a type of EC algorithm called quantum-inspired particle swarm optimization ("QPSO"), coupled with a random forest algorithm ("RF") as a wrapper method to build a prediction model that has high accuracy and a good balance between sensitivity and specificity. Inspired by wave functions in quantum physics, QPSO has enhanced searching ability and improved optimization results over many other commonly used EC algorithms; empirically, it is superior based on comparative experiments using benchmark test functions.

A training phase is an exploratory phase to build a model. Machine learning algorithms may use feasible or optimized methods for feature selection and classification. For a deep learning method, the model may be built on the extracted important features by automatically estimating the weights under the architecture of neural networks. In a non-limiting example, during the process of building a training model an n-fold cross validation (e.g. n-1 folds for building a model and 1 fold for evaluation) procedure may be used to check the robustness of the training model. After building a training model, an independent test set may be used to evaluate the model performance. The subjects in the test set should have similar characteristics as in the cohort with the same disease, but different from the training set.

I. Texture Features

Because of the heterogeneous natural history of IPF, a multidisciplinary team of pulmonologists, radiologists, and pathologists has devoted to build a guidance of diagnostic models of IPF for subjects with interstitial lung disease. According to the guidelines, a HRCT scan is required for diagnosis of IPF. Quantitative image analyses ("QIA") using texture-based features from HRCT scans have been utilized intensively in pulmonary related diseases. For example, QIA are used for robust classification of interstitial lung disease patterns. Scores from QIA can be a good representation of IPF disease severity. The models that leverage HRCT quantitative imaging data usually require measurement of changes from baseline to follow up. However, not many subjects have follow-up HRCT scans unless they have experienced shortness of breath or suspicion of progression. Given that HRCT scans are not utilized for monitoring purposes but for confirmation of progression, and subjects with IPF have short median survivals, it would be desirable to develop a prediction model for the IPF progression using only baseline HRCT scans.

Texture features extracted from images can be considered as a mathematical characterization of images. They reflect granular spatial information quantitatively. They may be used to describe the grey levels of voxels along different orientations as well as spatial relationships of voxels within a local neighborhood. Features can be extracted using a grid sampling procedure. In a non-limiting example, grids composed of 4-by-4 voxel squares may be placed contiguously. From each grid, a voxel may be selected. The grid sampling may be used to assure complete coverage of regions of interest.

In some configurations, a wrapper method is provided with a machine learning algorithm in the task of texture feature selection and classification. The methods described herein may provide markedly improved results for predicting the progression of IPF based on the texture features.

II. Feature Selection

In classification problems, an important step is to carefully select a small number of features for prediction. This selected subset of features can substantially reduce the processing time, and give robust and superior results to using the full set of features. Selecting a subset that gives the best performance in classification is challenging.

In feature selection, there are broadly two types of algorithms: filter methods and wrapper methods. Filter methods assess the relevance of features by looking only at the intrinsic properties of the data. For example, stepwise regression adds or eliminates individual variables sequentially until there is no statistically significant change in model performance. The selected variables then serve as inputs to the classification algorithm. Filter methods separate feature selection from classification, and typically, feature selection is performed only once before the classification task. The main advantage of filter techniques is that they are computationally simple and fast. However, filter methods ignore the interactions of the feature selection step with the classification step, which may result in a compromised classification performance.

Wrapper methods evaluate predictors holistically and may use procedures that add and/or remove predictors simultaneously, in order to find a combination that optimizes the performance. Wrapper methods treat different feature subsets as inputs and the performance of the models as outputs. An optimizer and a classifier may be used in wrapper methods. The metrics from the classifier may serve as the objective function for the optimizer to search the best feature subset. Compared to filter methods, wrapper methods are usually computationally expensive because many candidates of subsets have to be evaluated against the previous best subset. Wrapper methods may also have a higher risk of overfitting due to the lack of established criteria of a penalized function. On the other hand, wrapper methods are able to directly relate feature subsets to the classification performance. They may include the interaction between feature subset search and model selection, and they are able to take into account feature dependencies.

III. QPSO Optimizer in Wrapper Method

Evolutionary Computation ("EC") is a useful optimizer that may be used in wrapper methods to search the feature space and find feature subsets that optimize the classification performance. Particle swarm optimization ("PSO") is an EC algorithm that does not impose any assumption on the objective functions. PSO was inspired by swarm intelligence: a swarm collectively acts and communicates so that a good solution can be found quickly. There are many variants of PSO, and quantum PSO is one of them. Like basic particle movements in the quantum mechanics framework, QPSO is a global optimization algorithm with superior searching capabilities compared to other EC algorithms. It is different from traditional PSO algorithms in that particles have no trajectory, instead, the particles appear in positions with probabilities. The QPSO algorithm is suitable to be used for searching the feature space and find features due to its superior capability in searching high-dimensional space and its successful applications in real-world problems including those in the imaging field.

To prevent QPSO from premature convergence, an algorithm can use probabilistic crossover operations and random mutation operations, as crossover and mutation operators have shown to improve the PSO performance in feature selection. In some configurations, each particle in QPSO may be coded using a binary coding scheme. In a non-limiting example, a feature space may be selected to include 5 features and a particle may be encoded as (1, 0, 0, 1, 1). In this notation, the $1^{st}$, $4^{th}$, and $5^{th}$ features are included and the $2^{nd}$ and $3^{rd}$ are excluded in selection.

IV. Feature Selection and Classification

In some configurations, the classification model can be based on selected features using a random forest algorithm. Tree-ensemble-based machine learning techniques such as random forest are effective for solving real world problems. Random forest may be used in the medical imaging field and is highly successful in many classification tasks. For high-dimensional data, random forest is easily applicable in distributed systems. A random forest classifier may be computationally fast and reasonably easy to train for high-dimensional data, and may also minimize storage.

Re-sampling may be used as a pre-processing technique in statistics to enhance frequencies in minority classes to obtain a balanced performance in classification. Various re-sampling techniques have been developed in biomedical imaging studies, and any appropriate re-sampling technique may be used in accordance with the present disclosure. Re-sampling approaches may include up-sampling or down-sampling. Up-sampling is any technique that simulates or imputes additional data points, and down-sampling refers to any technique that reduces the number of samples to improve the balance across classes. In some configurations, a combination of over-sampling the minority class and under-sampling the majority class, such as a synthetic minority over-sampling technique ("SMOTE"), can achieve better classification performance than using either alone. In SMOTE, the over-sampling may be to sample "synthetic" examples with inversely proportional weights of sample size in order to balance the ratio of classes, rather than sampling with replacement. The majority class may be under-sampled by randomly removing samples from the population until the minority class becomes some user-specified percentage of the majority class. The SMOTE technique can be used on the training set, and independently the classifier may be applied to the test set to be consistent with the nature of the data. The resampled training data set may include balanced frequencies for progression and non-progression voxels.

In some configurations, a Quantum PSO-random forest ("QPSO-RF") algorithm can be implemented as an integrated wrapper algorithm that performs HRCT texture feature selection and imaging pattern prediction effectively. In a non-limiting example, the algorithm may a series of steps. First in the resampling step, the SMOTE technique can be used to resample the training set. Then, the QPSO can be used as the optimizer to search the feature subsets, and random forests may be built upon selected subsets which can produce the evaluation metrics. The iterative process of QPSO-RF searches the feature space in all the particle best and returns the global best at the last iteration as the best feature subset that gives the maximized objective function. QPSO-RF may use the QPSO to select features from a resampled data set to build a random forest classifier, and uses the objective function to guide the algorithm to find a best feature subset. The objective function to optimize in a QPSO-RF method may take the form:

$$\underset{F\theta}{\text{maximize}} \{\min(\text{sensitivity}, \text{specificity})\} \quad (1.1)$$

$$\text{sensitivity} = \frac{\sum_i^N y_i * \hat{p}_i}{\sum_i^N I(y_i = 1)}, \quad (1.2)$$

$$\text{specificity} = \frac{\sum_i^N (1 - y_i) * (1 - \hat{p}_i)}{\sum_i^N I(y_i = 0)}, \quad (1.3)$$

$$\text{accuracy} = \frac{\sum \hat{p}_i I(y_i = 1) + (1 - \hat{p}_i) I(y_i = 0)}{N}. \quad (1.4)$$

The maximization may be over all possible sets of selected texture features of $F_\theta$ from QPSO-RF with the minimum value of either sensitivity or specificity, $y_i$ is a binary variable that takes on value 1 if the $i^{th}$ voxel shows ground truth of progression and takes on the value 0 if the voxel is stable ($y_i=0$); N is the total number of voxels and $\hat{p}_i$ is the binary predicted probability from the model that the $i^{th}$ voxel becomes progressive in the next visit using the QPSO-RF model. The notation / is the indicator function.

To build a robust model for classification the intended usage for the population of interest may be taken into account. The characteristics of the independent test set used for prediction in the model may be selected to be similar to the training set. In a non-limiting example, both the prevalence of population and inclusion criteria for model building may be selected to be the same. Greater generalizability may be achieved by understanding the sources of measurement variations in data collection and ability to resolve or control the sources of variation by denoising or normalization methods. Data collection methods or the intended population of the training set may also influence the analytic validation and clinical validation. The quality and characteristics of training data set may be controlled for, or factors may be mitigated to normalize heterogeneous data to obtain generalizability in a test set or other utilities.

In some configurations, an integrated method is provided for the design of data collection in machine learning and model development for predicting disease progression with analytic evaluation and clinical evaluation. Multifactorial approaches may be used to solve problems that typically arise in imaging studies. Such situations include unbalanced rates of classifier (e.g. different prevalence rates), different sources of measurement variations from multicenter studies, requirements to simultaneous process the important feature selections, and the like. The methods may use a synthetic minority over-sampling technique, features from denoised images, particle swamp optimization with random forest classifier to overcome the inter-dependency between feature selection and the classification model, and the like. Inclusion and exclusion criteria in clinical trials may be used to determine the intended population to treat and used in labeling of a therapeutic product if such is shown to be effective. The characteristics of the training data set may influence the accuracy of prediction in a test set for a prediction model to perform accurately, so the methods may enforce similarity between the source of the training and test data sets. In some configurations, this may include the inclusion and exclusion criteria.

Figure 1B:
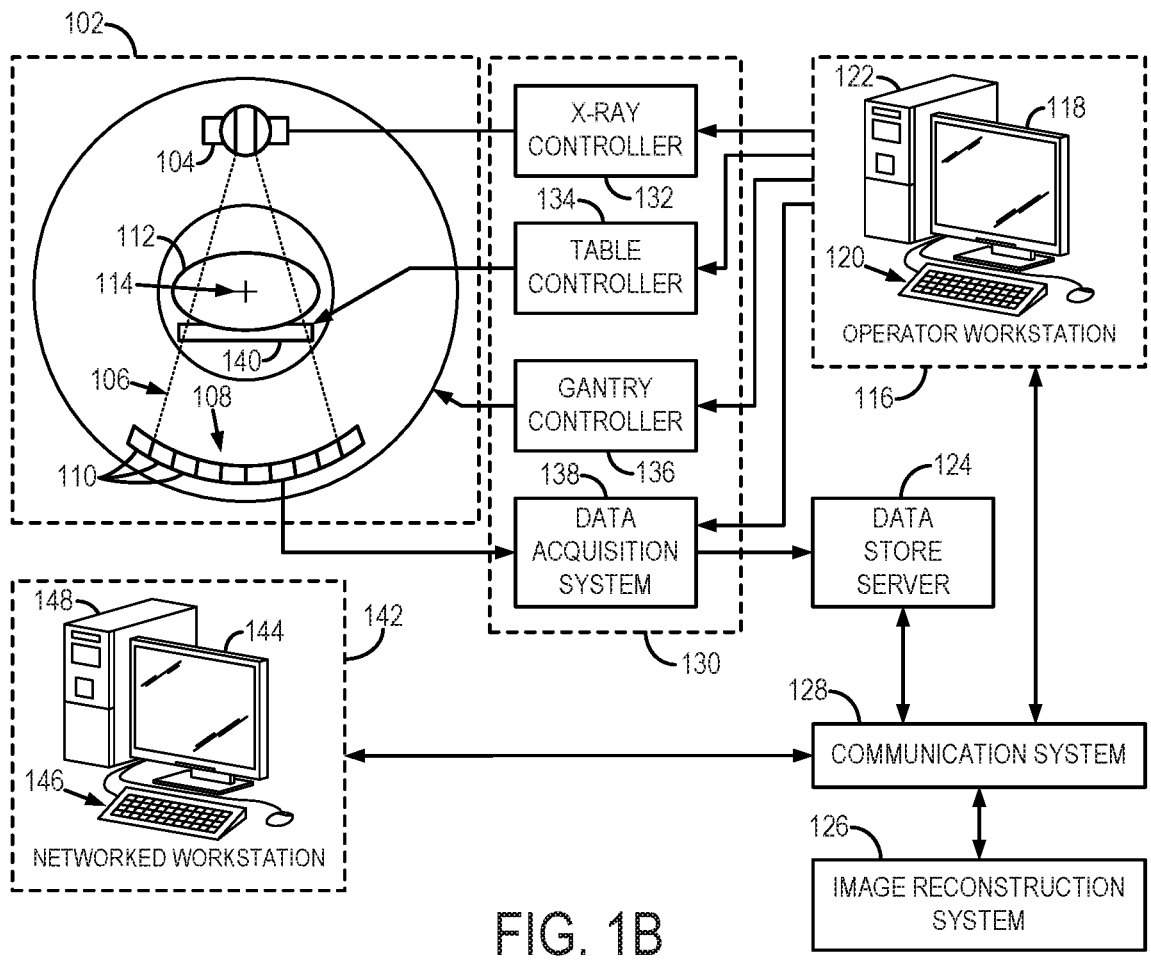

Referring to FIG. 1, a block diagram is shown of an example computed tomography ("CT") system that can implement the methods described in the present disclosure.

With initial reference to FIGS. 1A and CT imaging system 110, which employs an embodiment of the invention, includes a gantry 112 representative of a so-called "third generation" CT scanner. Gantry 112 has an x-ray source 113 that projects a fan beam (or cone beam) of x-rays 114 toward a detector array 116 on the opposite side of the gantry. The detector array 116 is formed by a number of detector elements 118 which together sense the projected x-rays that pass through a medical patient 115. Each detector element 118 produces an electrical signal that represents the intensity of an impinging x-ray beam and hence the attenuation of the beam as it passes through the patient. During a scan to acquire x-ray projection data, the gantry 112 and the components mounted thereon rotate about a center of rotation 119 located within the patient 115.

The rotation of the gantry and the operation of the x-ray source 113 are governed by a control mechanism 120 of the CT system. The control mechanism 120 includes an x-ray controller 122 that provides power and timing signals to the x-ray source 113 and a gantry motor controller 123 that controls the rotational speed and position of the gantry 112. A data acquisition system (DAS) 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 which stores the image in a mass storage device 129.

The computer 126 also receives commands and scanning parameters from an operator via console 130 that has a keyboard. An associated display 132 allows the operator to observe the reconstructed image and other data from the computer 126. The operator supplied commands and parameters are used by the computer 126 to provide control signals and information to the DAS 124, the x-ray controller 122, and the gantry motor controller 123. In addition, computer 126 operates a table motor controller 134 which controls a motorized table 136 to position the patient 115 in the gantry 112.

Figure 2:
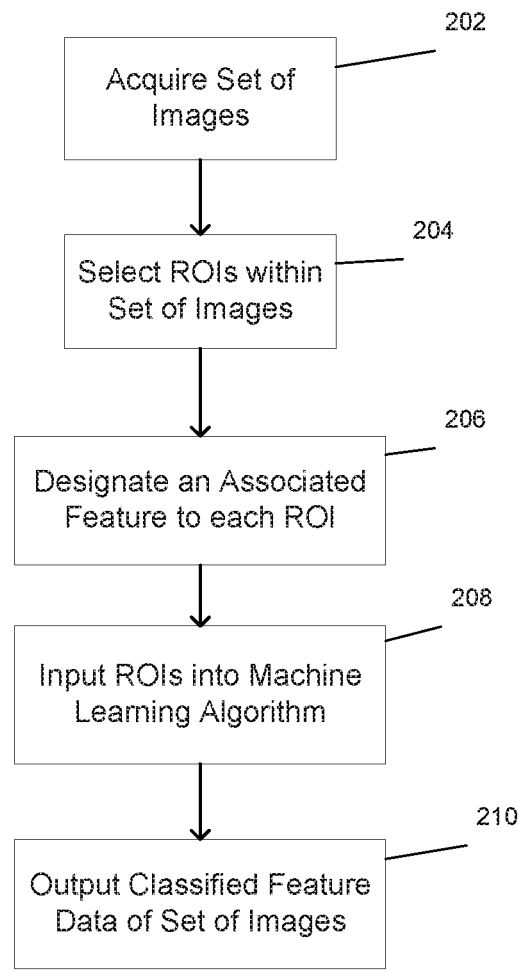
FIG. 2 is a flowchart setting forth the steps of training a machine learning algorithm.

Referring to FIG. 2, a flowchart is shown of non-limiting example steps for a method for training a machine learning algorithm to predict progression of IPF.

As indicated at step 202, a set of images can be acquired for a plurality of patients, or may be accessed from an image storage/repository. In a non-limiting example, the set of images can include CT images. The set of images can include a first set of images and a second set of images. The first set of images can be a baseline and the second set of images can be a follow-up scan. In a non-limiting example, the baseline scan and the follow-up scan can be taken approximately 6-12 months apart from each other. It is to be appreciated that any appropriate period of time between the baseline scan and the follow-up scan may be used.

As indicated at step 204, regions-of-interest ("ROI") are selected within the set of images. ROIs can be selected to avoid airways and blood vessels within the scan and selected to mark a square of voxel-wise sampling space. In a non-limiting example, the ROI can be a 4-by-4 sampling grid. Each of the ROIs may be selected to mark and collect textural information at the ROI.

As indicated at step 206, each ROI can be designated with a texture feature set. The feature set indicates the progression of a disease, such as pulmonary fibrosis. Each identified ROI in each scan reflects progression or non-progression of IPF. In a non-limiting example, to mark the ROIs as progression or non-progression, two paired longitudinal CT scans may be used, one from each of the first and second set of scans. Each paired HRCT images included the first set of images (e.g. baseline) and the second set of images (e.g. 6-12 months follow-up) that can be reviewed and compared to determine progression or non-progression of a disease, such as IPF. A medical professional reviewing and comparing two scans from the same patient, one from the first set of scans and one from the second set of scans, would know whether the ROI should be indicated as progression or non-progression, and marks an annotation on the first set of the images. For each of the set of scans, the corresponding scans in the first and second set of images may be registered with each other and the anatomical correspondence of the ROIs in both scans may be located.

As indicated at step 208, each ROI may be used to train a machine learning algorithm by inputting the ROIs and associated features into the machine learning algorithm. The algorithm can identify the ROIs as indicating regions of disease within the set of images based on the features. The machine learning algorithm can be trained using the one sub-set images that were taken as baseline images and the other sub-set of images that were taken as follow-up images can be used to test and further train the machine learning algorithm.

As indicated at step 210, classification probabilities can be generated as an output of the machine learning algorithm. The classification probabilities can include texture features that can be calculated based on local neighborhoods of voxels. In a non-limiting example, the texture features may be calculated at a voxel-by-voxel basis, taking neighborhoods of voxels together at a time. The trained machine learning algorithm can then be used to determine and generate a report indicating progression of a disease, such as IPF and the like, in an image.

Figure 3:
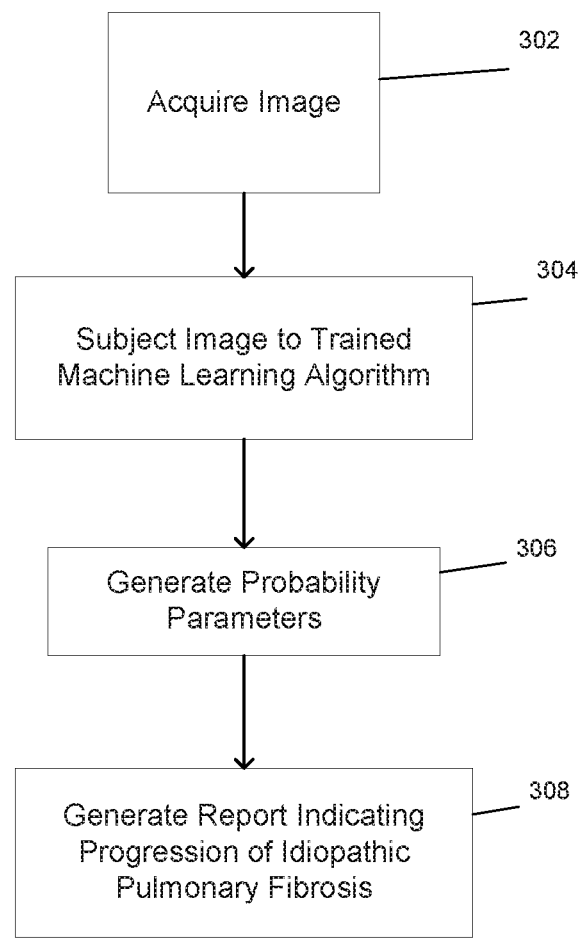
FIG. 3 is a flowchart setting forth the steps of generating a report indicating progression of idiopathic pulmonary fibrosis in an image.

Referring to FIG. 3, a flowchart is shown of non-limiting example steps for a method of determining and generating a report of the progression of IPF in an image. The method of FIG. 3 implements the trained machine learning algorithm of FIG. 2 to generate the report indicating progression of IPF.

As indicated in step 302, the method of generating a report that classifies and quantitatively detects the progression of IPF includes acquiring a CT image.

As indicated in step 304, the image can be subjected to the trained machine learning algorithm, that is trained according to the method described above with respect to FIG. 2. The output of the machine learning algorithm may include probabilities of expected progression over a certain period of time and quantitative parameters of the image. In a non-limiting example the period of time may include between 6 and 12 months.

As indicated in step 306, using the quantitative parameters and probabilities of progression from the machine learning algorithm, probability parameters can be generated by evaluating the quantitative parameters. The probability parameters can predict progression of IPF. The quantitative parameters indicate whether the classified regions indicate a progression or non-progression of IPF. The quantitative parameters can be relative to previous data of a patient whose image is being evaluated. The quantitative parameters indicate a probability of change in the progression of IPF of the patient.

As indicated in step 308, a report can be generated from the probability parameters and the quantitative parameters using a computer system. The report can indicate a quantitative analysis of the predicted probability of progression in the image of ranging 6 to 12 months in a subjects with IPF in a natural follow-up.

EXAMPLE 1

In one non-limiting example, a total of 50 anonymized HRCT images of subjects with IPF from a multi-center clinical trial were selected and at least two scans were available for each subject for the model building purpose. The data set was collected with well-characterized HRCT scans from subjects of IPF and the dates of baseline scan ranged from 2011 to 2015. Anonymized HRCT images of these subjects were archived at the UCLA Computer Vision and Imaging Biomarkers Laboratory. The use of anonymous image data was approved by local institutional review board. The population had a mean age of 65.9 years and a mean forced vital capacity ("FVC") percentage predicted value of 69.2%. The scans included a baseline scan and a 7.3 month (SE±1.6 months) follow-up HRCT scan from each subject with IPF. An outline of a non-limiting machine learning algorithm is shown at FIG. 4.

Statistical procedures were implemented to test if the differences of prediction accuracy between the proposed QPSO-RF and other comparator methods were statistically significant.

The multiple comparison was addressed using a Benjamini-Hochberg procedure controlling the false discovery rate ("FDR") at 0.05 significance level. In total, 23 pairwise comparisons of the proposed algorithm to comparators trained on resampled or original training data set.

The data was split into a training set and a test set. The training set had 26 subjects, and the test set had a different group of 24 subjects. The training set had 77 non-progression and 50 progression ROIs, adding up to 127 ROIs; at the voxel level, the training set had 1172 non-progression and 582 progression voxels, adding up to 1754 voxels. The test set had 101 non-progression and 22 progression ROIs, adding up to 123 ROIs; at the voxel level, the test set had 1605 non-progression and 336 progression voxels, adding up to 1941 voxels. The progression and non-progression lung morphology outcomes had an unbalanced ratio. At the voxel level the ratio was 1:3 (918 progression: 2777 non-progression instances) and at the ROI level the ratio was 1:2.5 (72 progression vs 178 non-progression). For the training set, the re-sampling SMOTE technique was applied as a class imbalance remedy; the post-SMOTE training set had 1746 progression and 1746 non-progression voxel instances and the model was trained on this re-sampled set. The test set was evaluated without any resampling modifications. Texture features were calculated at the voxel level and the radiologist references were ROI-based, and therefore performed a majority voting strategy to transform the classifier outcome from voxel to ROI level.

Comparing the performance with other feature selection and classification techniques required considering a wide range of characteristics. Firstly, a range of wrapper methods were considered that use different optimizers and classifiers. The classifiers used included support vector machine ("SVM") and shallow neural network ("NNET"); classifiers using all features (without feature selection) were also included in the comparison. The optimizers used for comparison included the basic version PSO and the Genetic Algorithm (GA). GA was inspired by the principles of genetics and evolution, and mimics the reproduction behavior observed in biological populations. The GA employs the "survival of the fittest" principle in its search process to select and generate individuals, for example feature subsets, that are adapted to their environment. The desirable traits tend to over-express over a number of generations (iterations), leading to better and better solutions. GA has also been frequently used in feature selection problems. Research has shown that PSO has the same effectiveness as a Genetic Algorithm ("GA") with significantly improved computational efficiency.

The method described herein was also compared to non-wrapper, model-based methods including LASSO and SCAD. LASSO and SCAD were used to perform feature selection by employing penalties. They have been widely adopted and can effectively enhance the prediction performance of the regression model.

The comparators used were compatible with the medical imaging field and have comparable computational efforts. The configurations of each comparator algorithm were set as follows. For LASSO and SCAD, the feature set was standardized and then used cross validation to choose the best penalty parameters for prediction. Then, the cross-validated LASSO or SCAD model was applied to the test set. For GA, 1000 iterations were used, 40 populations, crossover rate of 0.8 and mutation rate of 0.02, which was comparable to QPSO and PSO parameter settings. For SVM, a Gaussian radial basis function (RBF) kernel was used with a scaling factor 1. For NNET, a two-layer feedforward network was used with 10 hidden-layer neurons, a sigmoid transfer function in the hidden layer, and a softmax transfer function in the output layer. These parameters for the comparator optimizers and classifiers were pre-specified based on the computational feasibility consideration as well as best practices reported in literature.

The QPSO-RF algorithm yielded a model with 19 texture features and achieved 81.8% sensitivity, 82.2% specificity and 82.1% accuracy at the ROI level on the test set in predicting progression at 6 months to 1 year follow-ups. It is clear that QPSO-RF is superior compared to other wrapper methods and model-based methods, in a sense that QPSO-RF selects a smaller set of texture features than most of the other algorithms, has a higher and more balanced classification sensitivity and specificity, and has higher accuracy. Compared to LASSO, SCAD, other wrapper methods, and classification models without feature selection, QPSO-RF provides the only solution that both sensitivity and specificity achieves above 80%. It also achieves the highest classification accuracy with the smallest feature set. Using conditional logistic regressions and controlling the overall FDR at the significance 5% level, QPSO-RF accuracy is statistically significantly higher than all other methods except for the SVM without feature selection; the latter method is not ideal because it classifies all ROIs as non-progression. The QPSO-RF selected features include 2 summary statistical features, mean and mean32 (gray-level mean of 32 brightest voxels), and 17 gray-level co-occurrence matrices ("GLCM") features. These features are important to understand the characteristics of the images and are good representations of the images.

In addition, a re-sampling technique was helpful to achieve better classification results. There is no method that achieved above 80% for both sensitivity and specificity. The resampled QPSO-RF achieved statistically significantly higher classification accuracy than other methods. Generally, wrappers trained without resampling produced higher specificity, but much lower sensitivity and reduced overall accuracy compared with the wrappers trained with resampling. This is because the data without resampling has under-representative progressive class, and as a result, it's hard for the models to pick up the minority class. In particular, if QPSO-RF was applied without re-sampling, 30 features were selected and the sensitivity dropped to 72.7%, specificity dropped to 76.2%, with overall accuracy reduced to 75.6%. Compared to other algorithms, QPSO-RF without SMOTE still achieved one of the highest accuracy levels, balanced sensitivity and specificity, and select one of the smallest feature sets.

On the resampled data set, RF (without feature selection) and PSO-RF had the highest accuracy among all methods following QPSO-RF; on the data set without resampling, RF (without feature selection) had the highest classification accuracy, and QPSO-RF and PSO-RF also had higher accuracy than most other methods. These results suggest that RF is a superior classifier for this data set. Further, QPSO method was found to be the best optimizer for the data set, and it selected a parsimonious feature subset compared to PSO and GA optimizers. As a result, the resampled QPSO-RF was found to be clearly a superior method that achieved high accuracy, balanced sensitivity and specificity, with a smaller number of selected features.

The classification procedure included 6 ROI sample cases, each of which were constructed based on the coordinates of each voxel. The voxel locations enabled visualization of the voxel level classification within each ROI. The algorithm correctly classified ROI patterns in case 1-4 cases but misclassified in case 5 and 6. Case 1 was a non-progressive ROI in the second image, and QPSO-RF correctly classified 97.4% voxels as expected to be non-progression in the first set of image, which transformed to a "non-progression" label correctly to the ROI. Case 2 was a progressive ROI in the second image, and 83.3% voxels classified correctly as progression to the ROI using the texture features from the first set of image. Case 3 was another non-progressive ROI, with 83.3% voxels classified as non-progression and the case was correctly classified using the first set of image. Case 4 was a progressive ROI and 86.7% voxels were classified correctly and the case was correctly classified as a progression ROI. Case 5 was a progressive ROI at the second set of image. However, 62.5% voxels from the first set of image were classified as expected to be non-progressive, which transformed to a "non-progression" label to the ROI. Similarly, case 6 was a non-progressive ROI with 85.7% voxels of the first image misclassified as expected to be progressive.

In summary, the method worked well for the data set in that it outperformed other methods by giving higher accuracy, higher and more balanced sensitivity and specificity, with a smaller number of selected features. The ROI-based prediction provides insights beyond disease extent and visual parenchymal patterns of IPF.

EXAMPLE 2

In a second example, a study was conducted to predict progressive lung regions from CT images after 6 to 9 months of scanning in a natural follow-up of subjects with idiopathic pulmonary fibrosis (IPF) in advance of standard clinical deterioration. The impact of this prediction is to stratify subjects into those more likely to benefit from continuing drug therapy or from early referral to lung transplantation, or when appropriate, further estimate the relative therapeutic effect if a subject is on a treatment.

A machine learning approach was used with a collection of retrospective HRCT image data in subjects with IPF who were naïve to the treatments for 6-9 months. The study had two parts: a model was built to predict a progression at small region of interest (ROI) level; and the prediction was expanded using the model into the whole lung and produced a metric of likelihood of prediction in the interstitial lung disease (LPILD). Data collection included taking advantage of retrospective data. Paired HRCT images from baseline and at another follow-up between 6 to 9 months were presented to a thoracic radiologist. The expert was instructed to contour a region of interest in the baseline image by looking for the change assessment of stability or progression using the paired HRCT at baseline and follow-up. After collecting the training set of the ground truth of ROI progressive status, a machine learning algorithm was built to classify them into expected to be progressive or stable (e.g. not progressive). When there were no changes in the selected features and model estimates, the algorithm locked and ROIs from the independent test set (e.g. not part of training set) were used to evaluate the model performance of predicting progression as part of supervised learning.

The algorithm classified each grid in the parenchyma into two types, whether they were expected to be progressive into the whole lung or not. The metric of a likelihood of progression for the follow-up was calculated using the baseline scan as a percentage scale and called a LPILD score. The score was compared with the changes in radiographic outcome and lung function test. The changes in the quantitative lung fibrosis (QLF) score was used as radiographic outcomes. The percent predicted forced vital capacity (ppFVC) was used as a lung function performance measure.

Anonymized longitudinal HRCT images were retrospectively collected from 215 IPF subjects in multiple studies and the dates of baseline scans range from May 2011 to March 2015. The use of anonymous image data was approved by a local institutional review board. Each subject was supposed to have at least two scans for the model building and testing purposes. Such images were collected for IPF diagnosis purposes. Of the 215 IPF subjects, 22 were excluded because of image quality issues, lack of follow-up visits, or the follow-up visits were before 5 months or after 13 months from the baseline visits. The eligible cohort of 193 IPF subjects has a mean age of 70.0 years (SD±7.5 years), 73% male/27% female, with the percent predictive forced vital capacity (FVC) of 67.8% (SD±12.3%). The average time from baseline to follow-up visits was 7.6 months (SD±1.8 months). The baseline quantitative lung fibrosis (QLF) score was 15.4% (SD±8.7%). QLF is a classifier-model-derived score and is a measure of IPF disease extent. Subjects' HRCT image sets were randomly assigned with two stratifications of the expected to be progressive and stable rate with 40-50% and the ratio of 40% and 60% in training and test sets. The allocation of test sample size of 122 subjects was preserved to have an approximate 85% power to detect a normalized hazard ratio (HZ) of 2, corresponding to a prediction of progression from baseline scan to the next 6-9 months of visit at a two-sided significant level of 5%. Subsequently, a sample size of 71 subjects was set for the training set.

To predict a progression at follow-up, the reading paradigm in the traditional supervised approach was designed using the baseline and 6-9 months follow-up HRCT scans from subjects with IPF. The dominant area of radiological patterns of usual interstitial pneumonia in IPF was located peripherally in the lower or middle lobes of the right and left lungs. As part of disease progression assessment in patients with ILD, an expert thoracic radiologist provided a ground truth by having reviewed the baseline and follow-up scans side-by-side and visually identified the classical area of worsening at follow-up scan compared with baseline scan, and contoured a classic representative ROI on the baseline HRCT scan and labeled the ROI as either expected to be stable or expected to be progressive. In the training set, there were 434 annotated ROIs from 71 subjects to build the classifier. The 434 annotated ROIs included 193 (44.5%) progression ROIs and 241 (55.5%) non-progression ROIs; 149 (34%) ROIs are from the upper lung, 185 (43%) ROIs were from the middle lung, and 100 (23%) ROIs were from the lower lung. There were 423 ROIs (97%) that contained the partial or full peripheral of the lung (within 1 cm from the chest wall), which is consistent with the nature of the disease. In the test set, there were 434 annotated ROIs from 122 subjects to evaluate the classifier. The 549 annotated ROIs include 208 (37.9%) progression ROIs and 341 (62.1%) non-progression ROIs. The visual registration step was performed by the radiologist.

Statistical texture features, co-occurrence texture features, and run-length parameters were used in the present example. Prior to obtaining quantitative texture features, the heterogeneous HRCT imaging quality was mitigated from different acquisition parameters by denoising. Texture features from the original HRCT and denoised HRCT images were extracted for comparison. A square of approximately 4 mm-by-4 mm grid sampling was implemented to generate voxel instances within each ROI. A total of 191 texture features were calculated based on these local neighborhoods of voxels, where the size window for calculating texture feature was 12×12 voxels. The types of texture features included statistical features, run-length parameters, and co-occurrence parameters. Texture features were computed for voxels within ROIs.

The usual approach of machine learning with optimization first builds a classifier model and then uses it to build a systematic robust model. In the present example the ROIs and labels from the baseline HRCT information was used to predict the ROIs at follow-up scans by classifying them as progression ($y_i=1$) or stable ($y_i=0$) in the next follow-up visit.

After adjusting unbalanced rates of a classifier (e.g. prevalence) by using a synthetic minority over-sampling technique, QPSO was used as the optimizer to search the feature subsets and build random forests from the selected subsets that produce the evaluation metrics. The QPSO-RF searches for the feature space iteratively and returns the global best solution at the last iteration as the best feature subset that gives the maximized classification performance. The objective function minimized is indicated by equation 1.1.

The training model learned from small ROIs was applied to the whole lung. In the test set, there were 122 independent subjects to test the generated baseline metric at the whole lung level. Prediction in the whole lung level was applied to each grid of 4x4 non-overwrapping voxel using the QPSO-RF model. After implementing and calculating the feature selection and classification on the training set, the likelihood of progression in interstitial lung disease (LPILD) was estimated using the model for each subject.

A LPILD metric was obtained by: texture features selected by QPSO from denoised HRCT images were extracted; a random forest classifier was run, which was built on the QPSO selected features to obtain classification results for each sampled voxel; the number of progression voxels predicted by the classifier and total number of voxels were recorded; and the LPILD metric was calculated by dividing the former with the latter and noting that LPILD is a metric that only uses baseline imaging information.

For the independent test set, the LPILD metric was computed in the whole lungs after the whole lung was segmented by semi-automated tool from the HRCT images. LPILD metric was compared with two outcomes of changes in the percent predicted FVC and QLF scores. The QLF scores were based on the lung reticular patterns on a HRCT scan and they range from 0 to 100%. The minimal clinically important differences is 3-4% in the most severe lobe, where the most severe lobe was defined as the one with the largest QLF score at baseline. A change in 4% increase in QLF between baseline and the follow-up scans was used to evaluate LPILD score as a threshold of radiographic progression in IPF. Similarly, the reduction in percent predicted FVC of 10% was used to evaluate LPILD scores as a threshold of IPF progression in lung function. Cox proportional hazard regressions and ad-hoc log-rank analyses with a threshold of mean of LPILD score were performed using two outcomes of the QLF and the percent predicted FVC.

The machine learning method of the present example yielded a set of 18 texture features from the denoised HRCT images using QPSO-RF. The performance of the model ranged from approximately 70% in the training set and 65%-68% in the test set in terms of sensitivity, specificity, and accuracy using the texture features from the original HRCT images. Moreover, the performance of the model from the denoised texture features reached approximately 60-73% in the training set and 70% in the test set in terms of sensitivity, specificity, and accuracy. Independent training set from the original images and test set from the denoised images led to similar performance. A set of texture features was produced from the denoised HRCT images, which had superior robust results in the test set. At the same time, the model performed well for predicting a progressive ROI in the next visit given that the accuracy of the prediction using the baseline scan is a challenging problem.

The selected denoised features and the classification algorithm of QPSO-RF that was built for prediction in the whole lung level to obtain a LPILD score. Progression was determined based upon whether or not subjects had QLF scores increased by more than 4%. The non-progression group had a higher percentage of female, were slightly older, had lower QLF and higher percentage predicted FVC at baseline.

The changes in QLF scores had a trend with the LPILD scores. In one IPF subject with a LPILD of 49.1%, the subject had an increased QLF of 12.6% from baseline to 17.3% at 7-month follow-up, and had experienced a more than 10% drop (from 69% to 55%) in FVC percent predicted value. This may be considered as a progressive case.

A Cox regression model was used to determine whether the baseline metric LPILD was associated with the follow-up changes in progression-free survival. An imaging based outcome using the QLF score was assessed, and a pulmonary function test based outcome using the percentage predicted FVC was assessed. For the former, the event "progression" was defined by a 4% or more increment of QLF score and 10% or more reduction in the percent predicted FVC in the follow-up scan. The mean ($\pm$SE) of imaging based progression free survival was 7.6 ($\pm$0.2) months. The mean ($\pm$SE) of FVC based progression free survival was 8.0 ($\pm$0.4) months.

The Cox regression results show that LPLID was well correlated with the QLF changes in the follow-up scan. Higher LPILD was associated with higher risk of progression in a univariate analysis, with a normalized hazard ratio of 1.45 (p=0.027). In a multivariate analysis after adjusting for subjects' age and gender, the normalized hazard ratio was 1.53 (p=0.041). LPILD was well correlated with QLF based progression with the median of 6-7 month follow-ups. The LPILD was higher in the group that shows progression. LPILD, was statistically significant in univariate and multivariate Cox regression results. In addition, a log-rank test using LPILD cutoff at 40% showed statistical significance where the subjects with 40 or higher in LPILD had shorter radiologic progression free survival than those with less than 40 in LPILD.

In some configurations, a potential usage of the systems and methods is to provide a counterfactual scenario to estimate the probability of progression in ILD if a subject decides not continue with an effective treatment. A subject who experienced disease progression may not undergo the HRCT scanning in a clinic even though the likelihood of prediction for the next visits in 6-9 months at the time of routine care or diagnosis scan is useful. In such a scenario, prediction of disease progression can be derived from baseline or the prior scans when a subject does not experience disease progression. LPILD can predict the radiological progression or worsening with only a single HRCT scan.

In some configurations, the systems and methods may be used to predict disease progression using metrics from baseline scans for subjects with IPF. A design for data acquisition may provide the first data set of IPF prediction using baseline HRCT scans at ROI level. An integrated algorithm of texture feature selection and pattern prediction, may yield superior results in terms of high accuracy, balanced sensitivity and specificity, with a small feature subset for predicting parenchymal progression. A machine learning method, coupled with a hybrid of quantum particle swamp optimization and random forest algorithm that incorporates a reference truth of imaging, can result in a predictive model that effectively monitors disease progression in IPF patients, such as by using data from a retrospective study.

Figure 5:
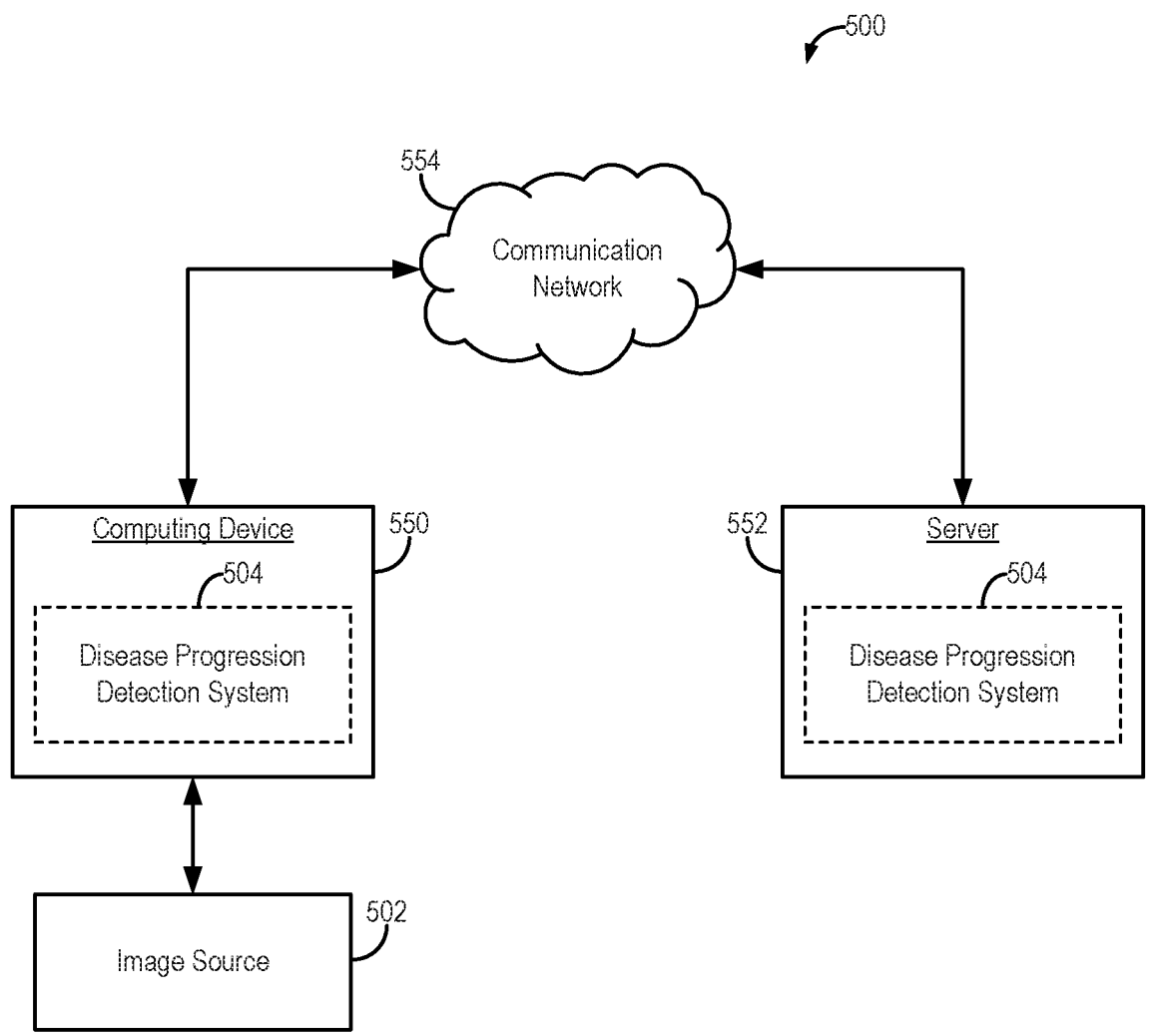
FIG. 5 is a block diagram of an example system that can implement a disease progression detection system for generating a report of disease progression using a hybrid machine learning and mechanistic model.

Referring to FIG. 5, an example of a system 500 for generating and implementing a hybrid machine learning and mechanistic model in accordance with some embodiments of the systems and methods described in the present disclosure is shown. As shown in FIG. 5, a computing device 550 can receive one or more types of data (e.g., CT, HRCT, ultrasound, MRI data, disease progression data, and the like) from image source 502. In some embodiments, computing device 550 can execute at least a portion of a disease progression detection system 504 to generate images of a progression of a disease from data received from the image source 502.

Additionally or alternatively, in some embodiments, the computing device 550 can communicate information about data received from the image source 502 to a server 552 over a communication network 554, which can execute at least a portion of the disease progression detection system 504 to generate images of a progression of a disease from data received from the image source 502. In such embodiments, the server 552 can return information to the computing device 550 (and/or any other suitable computing device) indicative of an output of the disease progression detection system 504 to generate images of a progression of a disease from the image source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as a CT system, an HRCT system, an ultrasound system, another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
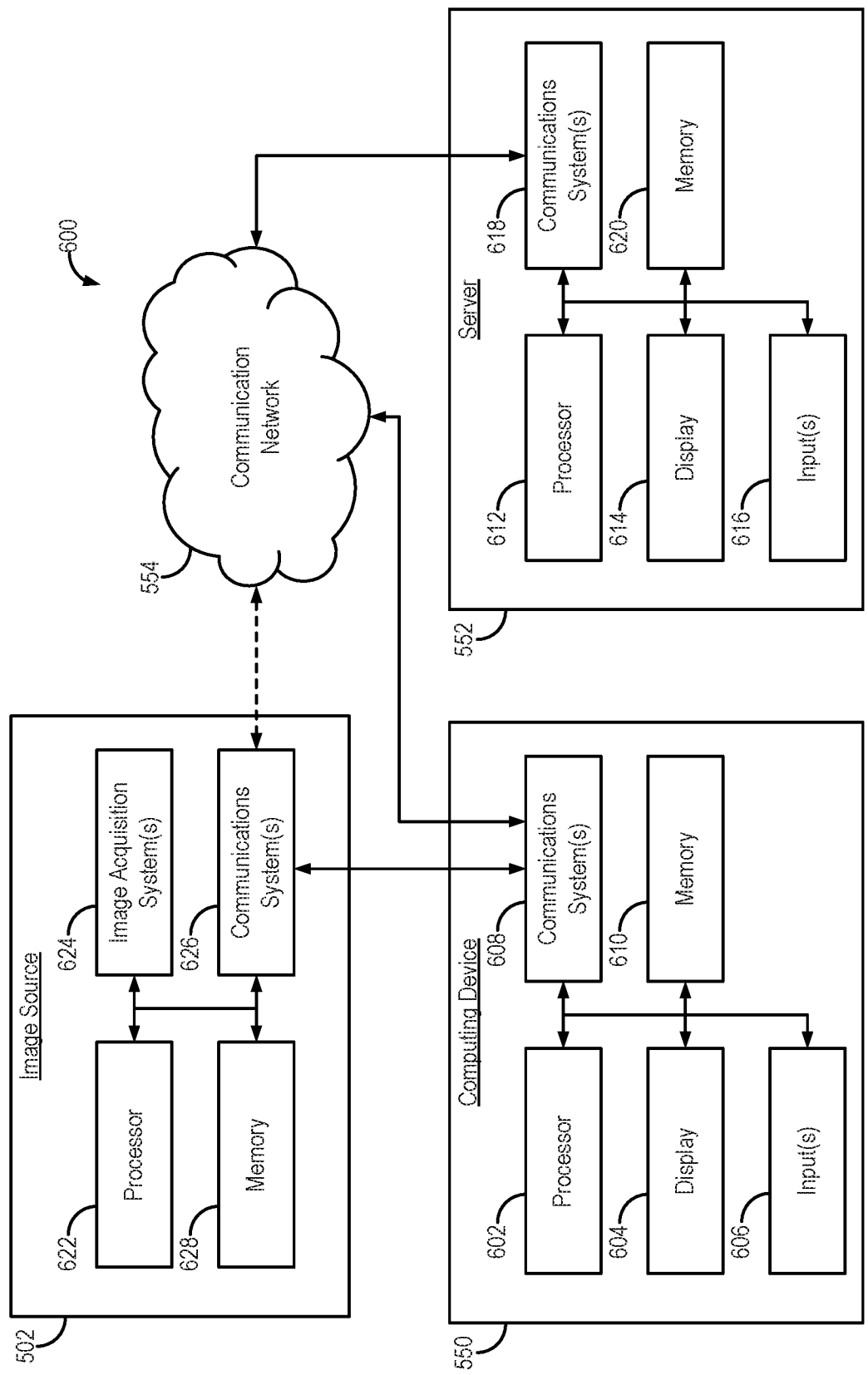
FIG. 6 is a block diagram of example hardware components of the system of FIG. 5.

Referring now to FIG. 6, an example of hardware 600 that can be used to implement image source 502, computing device 550, and server 554 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an RF transmission and reception subsystem of a CT system. Additionally or alternatively, in some embodiments, one or more image acquisition systems 624 can include any suitable hardware, firmware, and/or software for coupling to and/or controlling operations of a CT system. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A system that classifies predictive region-of-interest ("ROIs") of progression of idiopathic pulmonary fibrosis, the system comprising:
    a processor configured to analyze images of a patient and indicate regions in the images expected to reflect progressive pulmonary fibrosis in the future using a machine learning algorithm;
    a display to communicate the image of the patient indicating the regions in the images expected to reflect progressive pulmonary fibrosis in the future;
    a memory accessible by the processor and having stored thereon the machine learning algorithm, wherein the machine learning algorithm was trained by:
        (a) acquiring a set of computed tomography (CT) images of a plurality of patients;
        (b) selecting a plurality of ROIs within the set of images, wherein each of the ROIs designates a label indicating progression of pulmonary fibrosis;
        (c) training the machine learning algorithm by inputting the plurality of ROIs and the associated labels into the machine learning algorithm, wherein the machine learning algorithm identifies the ROIs in the set of images as indicating regions of pulmonary fibrosis within the set of images based on the features; and
        (d) generating classification probabilities from the output of the machine learning algorithm, wherein the classification probabilities classifies regions in the set of images as indicating regions of expected to be progressive pulmonary fibrosis in the future within the set of images.

2. The system of claim 1, wherein the set of images includes a first set of images and a second set of images, wherein the first set of images is a baseline and the second set of images are longitudinal to the first set of images, and wherein each of the plurality of patients have an image included in the first set of images and the second set of images.

3. The system of claim 2, wherein the first set of images and the second set of images are taken between 6 months to 12 months apart from one another.

4. The system of claim 2, wherein step (b) further includes:
identifying the ROIs as reflecting progression or non-progression by comparing an ROI from the first set of images to an ROI at the same location from the corresponding second set of images, wherein the image being compared from the first set and the second set are both related to the same patient.

5. The system of claim 1, wherein each ROI is chosen to avoid airways and blood vessels within the patient image.

6. The system of claim 1, wherein each ROI is evaluated at a voxel-by-voxel basis.

7. A method for generating a report that classifies and quantitatively detects progression of idiopathic pulmonary fibrosis, the method comprising:
(a) acquiring a computed tomography (CT) image;
(b) subjecting the image to a machine learning algorithm, wherein the machine learning algorithm is created by:
 (i) acquiring a set of CT images of a plurality of patients,
 (ii) selecting a plurality of ROIs within the set of images, wherein each of the ROIs designates an associated feature, the feature indicating progression of pulmonary fibrosis,
 (iii) inputting the plurality of ROIs and the associated features into the algorithm, wherein the algorithm identifies the ROIs in the images as indicating regions of pulmonary fibrosis within the images based on the associated features,
 (iv) generating classification probabilities from an output of the machine learning algorithm
 (v) generating quantitative parameters of the image, the quantitative parameters being indicative of idiopathic pulmonary fibrosis;
(c) generating probability parameters by evaluating the quantitative parameters, wherein the probability parameters predict progression of idiopathic pulmonary fibrosis; and
(d) generating a report from the probability parameters and the quantitative parameters using the computer system, wherein the report indicates a quantitative analysis of the progression of idiopathic pulmonary fibrosis.

8. The method of claim 7, wherein the classified feature data classifies regions in of the image as indicating regions of the expected to be progressive after 6 to 12 months in subjects with idiopathic pulmonary fibrosis.

9. The method of claim 7, wherein the set of images includes a first set of images and a second set of images, wherein the first set of images is a baseline and the second set of images is a follow-up of the first set of images, and wherein each of the plurality of patients have an image included in the first set of images and the second set of images.

10. The method of claim 9, wherein the first set of images and the second set of images are taken between 6 months to 12 months apart from one another.

11. The method of claim 9, wherein the first set is previous data from the subject, and wherein the report indicates a change in quantitative parameters relative to the previous data, indicating a change in the progression of idiopathic pulmonary fibrosis in the patient.

12. The method of claim 9, wherein step (b) further includes:
identifying the ROIs as reflecting progression or non-progression by comparing an ROI from the first set of images to an ROI from the second set of images, wherein the image being compared from the first set and the second set are both related to the same patient.

13. The method of claim 7, wherein each ROI is chosen to avoid airways and blood vessels within the patient image.

14. The method of claim 7, wherein each ROI is evaluated at a voxel-by-voxel basis.

15. The method of claim 7, wherein the generation of probability of progression between 6 and 12 months only requires the first set of images.

* * * * *